(12) United States Patent  (10) Patent No.: US 8,021,416 B2
Abrams  (45) Date of Patent: Sep. 20, 2011

(54) METHODS FOR DELIVERING A PROSTHESIS TO A SITE IN A BODY

(75) Inventor: Robert M. Abrams, Encinitas, CA (US)

(73) Assignees: Stryker Corporation, Kalamazoo, MI (US); Stryker NV Operations Limited, Dublin (IE)

( * ) Notice: Subject to any disclaimer, the term of this patent is extended or adjusted under 35 U.S.C. 154(b) by 526 days.

(21) Appl. No.: 11/036,028

(22) Filed: Jan. 14, 2005

(65) Prior Publication Data

US 2005/0121043 A1 Jun. 9, 2005

Related U.S. Application Data

(63) Continuation of application No. 10/001,538, filed on Nov. 14, 2001, now Pat. No. 6,846,316, which is a continuation of application No. 09/459,143, filed on Dec. 10, 1999, now Pat. No. 6,331,184.

(51) Int. Cl.
*A61F 2/84* (2006.01)
(52) U.S. Cl. ...................................................... 623/1.23
(58) Field of Classification Search .................. 606/108, 606/200; 623/1.23, 1.11–1.13
See application file for complete search history.

(56) References Cited

U.S. PATENT DOCUMENTS

| | | | |
|---|---|---|---|
| 4,364,392 A | 12/1982 | Strother et al. | |
| 5,108,407 A | 4/1992 | Geremia et al. | |
| 5,151,105 A | 9/1992 | Kwan-Gett | |
| 5,171,259 A | 12/1992 | Inoue | |
| 5,263,964 A * | 11/1993 | Purdy | 606/200 |
| 5,282,824 A | 2/1994 | Gianturco | |
| 5,334,210 A * | 8/1994 | Gianturco | 606/151 |
| 5,454,833 A | 10/1995 | Boussignac et al. | |
| 5,507,757 A | 4/1996 | Sauer et al. | |
| 5,522,836 A * | 6/1996 | Palermo | 606/200 |
| 5,591,195 A | 1/1997 | Taheri et al. | |
| 5,690,667 A | 11/1997 | Gia | |
| 5,782,860 A | 7/1998 | Epstein et al. | |
| 5,836,968 A * | 11/1998 | Simon et al. | 606/200 |
| 5,948,191 A | 9/1999 | Solovay | |
| 5,976,174 A * | 11/1999 | Ruiz | 606/213 |
| 6,063,104 A * | 5/2000 | Villar et al. | 606/213 |
| 6,063,112 A * | 5/2000 | Sgro | 623/1.12 |
| 6,168,617 B1 * | 1/2001 | Blaeser et al. | 623/1.11 |
| 6,254,612 B1 * | 7/2001 | Hieshima | 606/108 |
| 6,375,668 B1 * | 4/2002 | Gifford et al. | 606/200 |

FOREIGN PATENT DOCUMENTS

| | | |
|---|---|---|
| EP | 0508473 | 10/1992 |
| WO | 9724080 | 7/1997 |
| WO | WO 99/30640 | 8/1999 |
| WO | 0126707 | 4/2001 |

OTHER PUBLICATIONS

EPO Partial Search Report for EP Application No. 00982531.6, PCT/US0033321, Applicant Boston Scientific Limited, forms EPO 1507.4 03.95, 1503 03.82 and P0459 dated Mar. 28,2007 (4 pages).

* cited by examiner

*Primary Examiner* — Ryan J Severson
(74) *Attorney, Agent, or Firm* — Vista IP Law Group LLP

(57) ABSTRACT

An endoprosthesis cover may be attached to the distal end of a delivery device. The cover may be generally cylindrical in shape and may have a lumen through it. An endoprosthesis may then be covered as it is delivered to a treatment site.

20 Claims, 3 Drawing Sheets

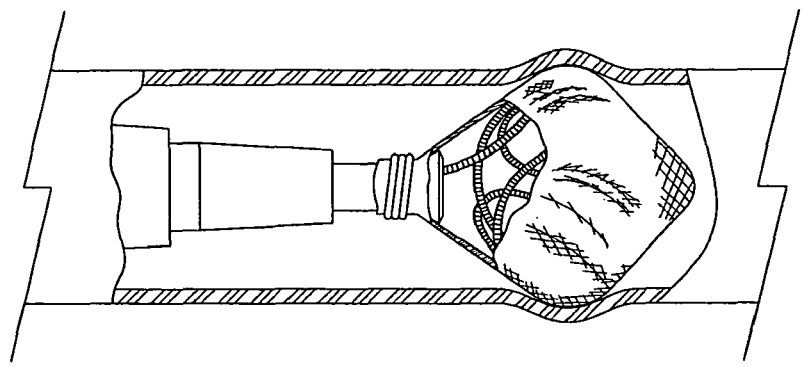
PRIOR ART   FIG. 1
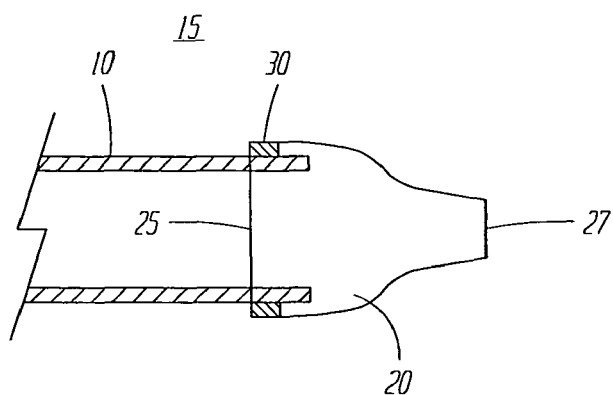
FIG. 2
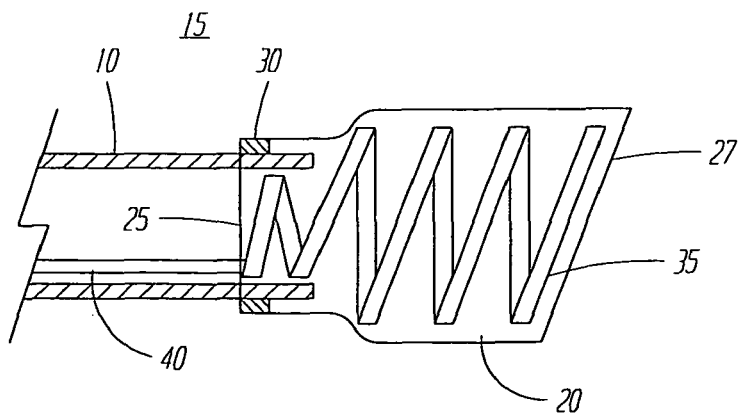
FIG. 3

METHODS FOR DELIVERING A PROSTHESIS TO A SITE IN A BODY

RELATED APPLICATION DATA

This application is a continuation of application Ser. No. 10/001,538, filed Nov. 14, 2001, now U.S. Pat. No. 6,846,316, which is a continuation of application Ser. No. 09/459,143, filed Dec. 10, 1999, now U.S. Pat. No. 6,331,184.

FIELD OF THE INVENTION

The present invention generally relates to devices implanted within the human body and further to coverings about those devices. Specifically, the present invention relates to a detachable system for covering an implantable devices as it is delivered into the human body. Those skilled in the art will recognize the benefits of applying the present invention to similar fields not discussed herein.

BACKGROUND OF THE INVENTION

A variety of devices are now commercially available for implantation through minimally invasive techniques. These devices include stents and stent-grafts used to maintain patent flow in blood vessels, the endo-biliary system or the urinary system. These stents and stent grafts have several different forms. Some are in the form of coiled wires while others are made from slotted tubes. Stents are also generally self-expanding or balloon expandable. Typically, they are made from metal and have a few important characteristics. These characteristics include expanded hoop strength, expansion force, expanded and unexpanded diameter, and the amount of foreshortening during expansion. Obviously the art of stent design is to work with these conflicting characteristics in such a way as to form the ideal stent. That stent would require very little force to expand, start with a very small unexpanded diameter and reliably expand to whatever diameter desired and the stent would not foreshorten when expanded.

Another important characteristic of a stent or stent-graft is the amount of expanded stent material that comes into contact with the vessel. Having the surface of the stent in contact with the stent is important because of in-stent restenosis. In-stent restenosis is a phenomenon where, for some reason, the vessel grows through the struts or between the coils and thereby obstructs fluid flow in the vessel. Where the stent is in direct contact with the vessel, the vessel can not impinge on the fluid flow. There is, therefore, a need for a stent which maximizes all of the characteristics above and has as close to 100% vessel contact in the area that is stented as possible.

Another type of device may generally be characterized as aneurysm repair devices. Depending upon where in the body the aneurysm is located, a ruptured aneurysm may be fatal. Typically aneurysm repair devices are used to prevent the aneurysm from getting larger and ultimately bursting. Exemplary types of aneurysm repair devices include those which protect the aneurysm from getting larger by shielding the aneurysm from fluid pressure, covering the neck of an aneurysm, or filling the aneurysm with some sort of packing material. Similar to stents, aneurysm repair devices have a variety of conflicting material characteristics which make them perform better, most notably surface contact or sealing capability. In addition, present coil-shaped repair devices have a potential for the leading edge of the coil to corkscrew into the vessel wall. There is therefore a need for an aneurysm repair device that has good sealing characteristics and one which would be less likely to corkscrew into the vessel wall.

U.S. Pat. No. 5,334,210 describes a prior art vascular occlusion assembly and is depicted in FIG. 1 of the current application. The assembly comprises a foldable material occlusion bag which is filled with a flexible filler. Because the material is not non-compliant, it must be folded and must therefore disadvantageously increase the profile of the device. This bag may be positioned in a blood vessel and is intended to stop fluid from flowing through the vessel. There is therefore no lumen in the device.

Overall there is need for a prosthesis which has nearly complete vessel wall contact while maintaining a patent fluid channel. This prosthesis and its accompanying delivery system would be highly advantageous.

SUMMARY OF THE INVENTION

The present invention overcomes the deficiencies of the prior art by providing a sheath attached to the distal end of a delivery device. The sheath may be generally cylindrical in shape and have a lumen therethrough. The sheath may be expandable such that, as an endoprosthesis is delivered into the lumen of the sheath, the sheath will take on the exterior configuration of the endoprosthesis. The endoprosthesis is thereby covered while maintaining a patent fluid lumen. The sheath may further be detachable from the delivery device and may have holes or slots to enhance blood porosity and to enhance its distensability. The endoprosthesis may include stents, coils, stent grafts, aneurysm repair devices or any other endoprosthesis known in the art.

BRIEF DESCRIPTION OF THE DRAWINGS

FIG. 1 depicts a prior art device.
FIG. 2 illustrates a first embodiment of the delivery system.
FIG. 3 depicts a partially deployed coil with the delivery system.

DETAILED DESCRIPTION OF THE INVENTION

Figure 4:
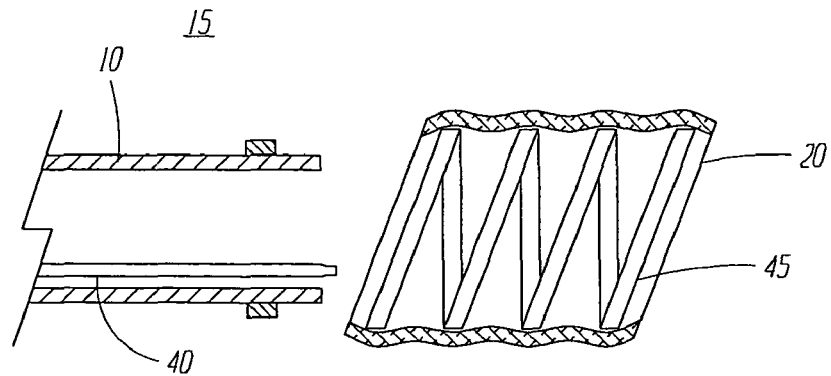
FIG. 4 depicts a fully deployed stent in a body lumen.

The following detailed description should be read with reference to the drawings in which like elements in different drawing are numbered identically. The drawings, which are not necessarily to scale, depict selected embodiments and are not intended to limit the scope of the invention.

Examples of constructions, materials, dimensions, and manufacturing processes are provided for selected elements. All other elements employ that which is known to those skilled in the field of the invention. Those skilled in the art will recognize that many of the examples provided have suitable alternatives that may also be used.

Turning now to FIG. 1. Delivery system 15 includes tube 10. Tube 10 may be a micro-catheter, guide catheter, hypotube or any other type of tube commonly known in the art. Depending on the application, the inner diameter or tube 10 may be 0.008-0.39 inches. Tube 10 may be formed of a polymer or a combination of polymers, metal, a metal polymer composite, a combination of polymers and metallic braid (not shown). Surrounding a distal portion of tube 10 is sheath 20. Sheath 20 may preferably be made of an elastomer or other highly compliant polymer. Such polymers may include latex, styrenic block copolymers such as SBS and SEBS made by Shell under trade name of Kraton, polyether-ester block copolymers (COPE) for co-polyesters made by DuPont under the trade name of Hytrel, thermoplastic polyamide elastomers (PEBA) made by Atochem under the trade name of Pebax, and thermoplastic polyurethane elastomer (TPUR) made by Dow under the trade name Pellathane, or thermoplastic polyolefin elastomers (TPOs).

Sheath 20 may further include a proximal opening 25 and a distal opening 27. In its non-distended configuration, sheath 20 may generally form a cylinder. Sheath 20 may have a ridge (not shown) on its interior near distal opening 27 which may be configured to better capture the distal end of a prosthesis. In an alternative embodiment, sheath 20 may have slots or holes (not shown) which would enhance the porosity of sheath 20 and provide better flexibility.

Sheath 20 may be frictionally fit about the distal end of tube 10. In a preferred embodiment, an adhesive bond 30 binds sheath 20 to tube 10. Sheath 20 may detach from tube 10 in a variety of ways. Where sheath 20 is frictionally fit over tube 10, detachment may be achieved simply by overcoming the frictional forces between sheath 20 and tube 10, e.g. pushing a prosthesis out of the distal end of tube 10. Where sheath 20 is attached to tube 10 by adhesive bond 30, the adhesive may be engineered to detach at any desired force. Adhesive bond 30 may be formed with any medically approved adhesive. In an alternative embodiment, sheath 20 may have a circumferential perforation distal of adhesive bond 30 and thereby provide sheath 20 with a tear away detachment mechanism.

Turning now to FIG. 3. Delivery system 15 is shown with a partially deployed self expanding coil 35. Coil 35 may be attached to pusher wire 40. When pusher wire 40 is moved distally relative to tube 10, the distal portion of coil 35 engages the distal portion of sheath 20. Sheath 20 then distends distally has coil 35 is advanced further out of tube 10. Once the entire coil 35 has been pushed out of tube 10, pusher wire 40 may be electrolytically detached. Methods of electrolytic detach are describe in U.S. Pat. No. 5,122,136 which is hereby incorporated by reference. It may further be appreciated that a variety of detach mechanisms are available to serve this function and furthermore that pusher wire 40 does not need to be attached to coil 35.

Figure 5:
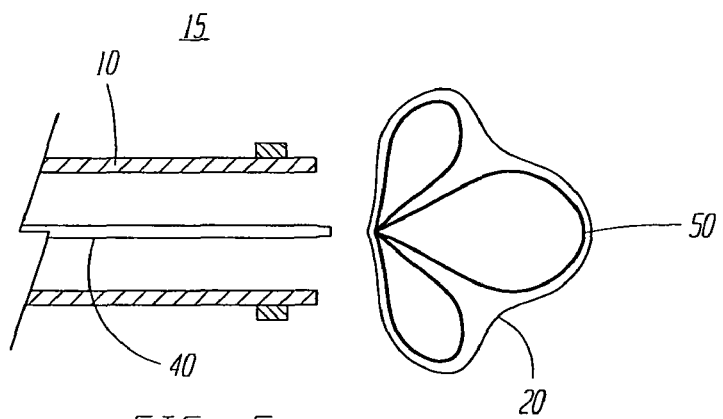
FIG. 5 illustrates a second endoprosthesis.

FIG. 4 depicts delivery system 15 in use in the vasculature. In this embodiment, a self-expanding stent 45 has been introduced into a blood vessel. Pusher 40 has been advanced such that stent 45 was forced out of tube 10 and into contact with the interior of sheath 20. After sheath 20 detached from tube 10, sheath 20 remains in place about stent 45 and prevents any incursion by the surrounding tissue into the lumen of stent 45 and thereby maintains a patent fluid lumen for blood to flow through. Another embodiment is depicted in FIG. 5 where a tulip shaped coil 50 is placed in a body lumen.

Figure 6:
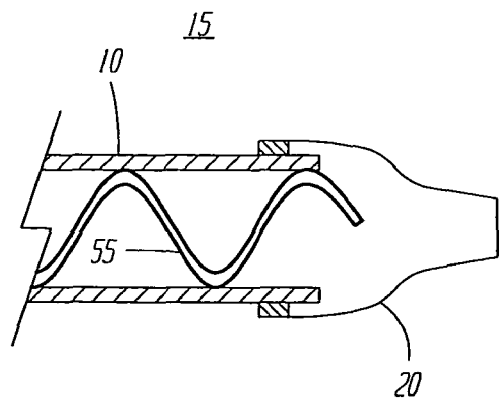
FIG. 6 illustrates a third endoprosthesis.

FIG. 6 illustrates yet another embodiment where wire 55 is advanced through tube 10. Wire 55 may be formed of any suitable medically approved metal such as stainless steel or alloys of nickel such as Nitinol. Wire 55 has a pre-curved shape and is only forced out of that shape by placing wire 55 into tube 10. Care should be taken to choose a material for sheath 20 which will conform to the pre-curved shape of wire 55 without deforming wire 55.

Figure 7:
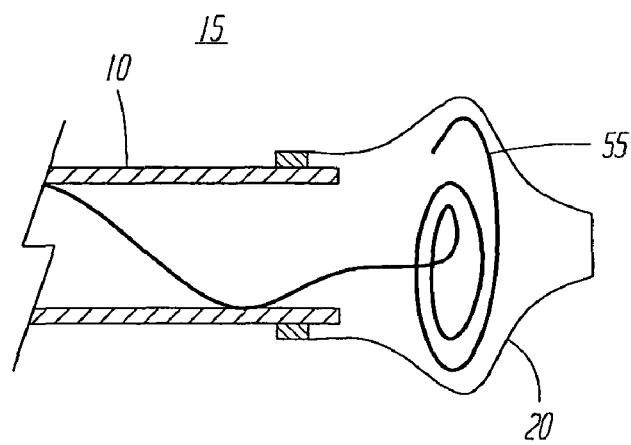
FIG. 7 depicts the third endoprosthesis partially deployed.
Figure 8:
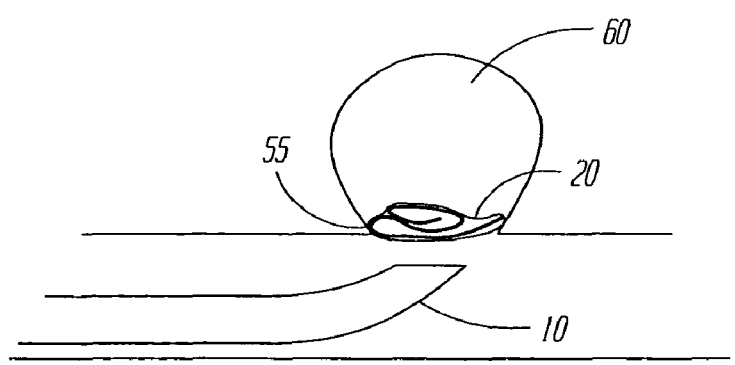
FIG. 8 illustrates the third endoprosthesis fully deployed in an aneurysm neck.

As can readily be appreciated from FIG. 7, as wire 55 emerges from tube 10 it enters sheath 20 and resumes its pre-curved shape. In this embodiment, wire 55 is pre-curved into a flat disc-like shape but could be any of a variety of shapes known in the art. As described above, further advancement of wire 55 eventually detaches sheath 20 from tube 10 and thereby delivers pre-curved wire 55 into a desired location with sheath 20 surrounding wire 55. FIG. 8 depicts a particular use of pre-curved wire 55. In this embodiment wire 55 forms into a disc-like shape suitable for covering an aneurysm neck. Wire 55 may be delivered without any other structure being placed into aneurysm 60. Alternatively, wire 55 may be delivered after particles or other embolic materials (not shown) have been deployed into aneurysm 60. In another embodiment wire 55 may be delivered into aneurysm 60 and particles may be delivered through wire 55 thereby filling aneurysm 60 and capping it with wire 55.

While the specification describes the preferred designs, materials, methods of manufacture and methods of use, those skilled in the art will appreciate the scope and spirit of the invention with reference to the appended claims.

I claim:

1. A method for delivering a prosthesis to a site in a body, comprising:
   providing a delivery system comprising a tubular member having a sheath releasably affixed to a distal end of the tubular member, said sheath having a distal opening and a lumen therethrough, said distal opening and said lumen of sufficient size to maintain patent blood flow through the lumen;
   advancing the tubular member through a vessel in a body to position the tubular member distal end at a site in the body;
   advancing a prosthesis which is not within the sheath, through an opening in the tubular member distal end and into the sheath, the delivery of the prosthesis into the sheath causing the sheath to release from the tubular member, such that the sheath containing the prosthesis is delivered to the site; and
   maintaining patent blood flow through the lumen and through the distal opening while said sheath is positioned at the site in the body.

2. The method of claim 1, wherein the site is an aneurysm neck.

3. The method of claim 1, wherein the site is an aneurysm.

4. The method of claim 1, wherein the sheath comprises a plurality of slots or holes.

5. The method of claim 1, wherein the sheath is frictionally fit to the distal end of the tubular member.

6. The method of claim 1, wherein the sheath is affixed by an adhesive bond to the distal end of the tubular member.

7. The method of claim 1, wherein the prosthesis expands as it is advanced out of the tubular member opening and into the sheath.

8. The method of claim 7, wherein the sheath distends to conform to the expanded prosthesis.

9. The method of claim 1, the prosthesis comprising an occlusive coil that is advanced through the tubular member using a pusher wire, and wherein the coil is electrolytically detached from the pusher wire once the coil is advanced out of the tubular member and into sheath.

10. A method for delivering a prosthesis to a site in a body, comprising:
    providing a delivery system comprising a tubular member having a delivery lumen in communication with an opening in the tubular member, and a sheath having a proximal end releasably affixed to an exterior of the tubular member proximate the opening, said sheath having a distal opening and a lumen therethrough, said distal opening and said lumen of sufficient size to maintain patent blood flow through the lumen;
    advancing the tubular member through a vessel in a body to position the opening proximate a site in the body;
    advancing a prosthesis which is not within the sheath, through the delivery lumen, out the opening, and into the sheath, the delivery of the prosthesis into the sheath causing the sheath to release from the tubular member, such that the sheath containing the prosthesis is delivered to the site; and maintaining patent blood flow through the lumen and through the distal opening while said sheath is positioned at the site in the body.

11. The method of claim 10, the prosthesis expanding as it is advanced out of the tubular member opening and into the sheath, wherein the sheath distends to conform to the expanded prosthesis.

12. The method of claim 10, the prosthesis comprising a pre-curved wire that forms a disc-like shape suitable for covering an aneurysm neck when delivered into the sheath.

13. The method of claim 10, wherein the site is an aneurysm neck.

14. The method of claim 10, wherein the site is an aneurysm.

15. The method of claim 10, wherein the sheath comprises a plurality of slots or holes.

16. The method of claim 10, wherein the sheath is frictionally fit to the distal end of the tubular member.

17. The method of claim 10, wherein the sheath is affixed by an adhesive bond to the distal end of the tubular member.

18. A method for delivering a prosthesis to a site in a body, comprising:

providing a delivery system comprising a tubular member having a delivery lumen in communication with a distal opening in the tubular member, and a sheath having a proximal end releasably affixed to an exterior of the tubular member around the distal opening, said sheath having a distal opening and a lumen therethrough, said distal opening and said lumen of sufficient size to maintain patent blood flow through the lumen;

advancing the tubular member through a vessel in a body to position the distal opening proximate a site in the body;

advancing a prosthesis which is not within the sheath, through the delivery lumen, out the distal opening, and into the sheath, the prosthesis expanding as it is advanced out of the tubular member opening and into the sheath, the sheath conforming to the expanded prosthesis, the advancing of the prosthesis causing the sheath to release from the tubular member; and maintaining patent blood flow through the lumen and through the distal opening while said sheath is positioned at the site in the body.

19. The method of claim 18, further comprising detaching the sheath from the tubular member as the prosthesis is deployed.

20. The method of claim 18, wherein the site is an aneurysm.

* * * * *